(12) United States Patent
Samproni

(10) Patent No.: US 10,921,280 B2
(45) Date of Patent: Feb. 16, 2021

(54) READER DEVICE AND METHOD OF SIGNAL AMPLIFICATION

(71) Applicant: Siemens Healthcare Diagnostics Inc., Tarrytown, NY (US)

(72) Inventor: Jennifer A. Samproni, Braintree, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 16/434,686

(22) Filed: Jun. 7, 2019

(65) Prior Publication Data

US 2019/0285568 A1 Sep. 19, 2019

Related U.S. Application Data

(60) Division of application No. 15/441,518, filed on Feb. 24, 2017, now Pat. No. 10,330,630, which is a (Continued)

(51) Int. Cl.
*G01N 27/327* (2006.01)
*C25B 9/18* (2006.01)
(Continued)

(52) U.S. Cl.
CPC ......... *G01N 27/3277* (2013.01); *C12Q 1/004* (2013.01); *C25B 9/18* (2013.01);
(Continued)

(58) Field of Classification Search
CPC .......................................... G01N 27/327–3278
(Continued)

(56) References Cited

U.S. PATENT DOCUMENTS 6,284,125 B1 9/2001 Hodges et al.
6,338,790 B1 1/2002 Feldman et al.
(Continued)

FOREIGN PATENT DOCUMENTS

CN 1967233 A 5/2007
CN 101368926 A 2/2009
(Continued)

OTHER PUBLICATIONS

European Search Report and Opinion of European Application No. EP 13810292 dated Nov. 24, 2015.
(Continued)

*Primary Examiner* — Bach T Dinh
(74) *Attorney, Agent, or Firm* — Dunlap Codding P.C.

(57) ABSTRACT

Fluid collection devices, analysis instruments and methods for making and using same are disclosed. The fluid collection device is provided with a device and an electrochemical cell. The device has first and second walls defining a microfluidic channel, and a sample application port communicating with the microfluidic channel. The first wall and the second wall are spaced a distance less than 150 microns. The electrochemical cell is disposed on the first wall to contact a sample travelling through the microfluidic channel. The electrochemical cell comprising molecule receptors such that a physical property of the first electrochemical cell is effected upon one or more of the molecule receptors binding to an electroactive species within the sample.

20 Claims, 3 Drawing Sheets

Related U.S. Application Data continuation of application No. 14/409,771, filed as application No. PCT/US2013/048108 on Jun. 27, 2013, now abandoned.

(60) Provisional application No. 61/665,353, filed on Jun. 28, 2012.

(51) Int. Cl.
  *C12Q 1/00* (2006.01)
  *G01N 33/487* (2006.01)
  *G01N 33/49* (2006.01)

(52) U.S. Cl.
  CPC ... *G01N 27/3272* (2013.01); *G01N 33/48707* (2013.01); *G01N 33/492* (2013.01); *G01N 33/4915* (2013.01); *Y10T 29/49117* (2015.01)

(58) Field of Classification Search
  USPC ..... 204/403.01–403.15; 205/777.5–778, 792
  See application file for complete search history.

(56) References Cited

U.S. PATENT DOCUMENTS

| | | | |
|---|---|---|---|
| 6,670,115 B1 | 12/2003 | Zhang | |
| 7,608,175 B2 | 10/2009 | Hodges et al. | |
| 2005/0013731 A1* | 1/2005 | Burke | G01N 33/558 422/400 |
| 2005/0077176 A1 | 4/2005 | Hodges et al. | |
| 2005/0150762 A1* | 7/2005 | Butters | C12Q 1/001 204/403.01 |
| 2005/0164328 A1 | 7/2005 | Kuwabata et al. | |
| 2005/0178674 A1 | 8/2005 | Hyland et al. | |
| 2005/0249606 A1 | 11/2005 | Rush | |
| 2007/0264721 A1 | 11/2007 | Buck | |
| 2007/0266871 A1 | 11/2007 | Wegner | |
| 2008/0202928 A1 | 8/2008 | Hyun et al. | |
| 2009/0145778 A1 | 6/2009 | Allmendinger | |
| 2009/0297574 A1 | 12/2009 | Ahn et al. | |
| 2010/0096276 A1 | 4/2010 | Kojima et al. | |
| 2010/0267161 A1 | 10/2010 | Wu et al. | |
| 2012/0067742 A1 | 3/2012 | Lee | |
| 2012/0080326 A1 | 4/2012 | Chatelier et al. | |

FOREIGN PATENT DOCUMENTS

| | | |
|---|---|---|
| CN | 101675338 A | 3/2010 |
| DE | 102005007539 A1 | 8/2006 |
| EP | 2778668 A1 | 9/2010 |
| JP | H04118554 A | 4/1992 |
| JP | H08327582 A | 12/1996 |
| JP | 2003529765 A | 10/2003 |
| JP | 2007507711 A | 3/2007 |
| JP | 2007163499 A | 6/2007 |
| JP | 2011099849 A | 5/2011 |
| KR | 1020010085902 A | 9/2001 |
| RU | 2002124858 A | 3/2004 |
| RU | 2263904 C2 | 11/2005 |
| RU | 70580 U1 | 1/2008 |
| RU | 2359038 C2 | 6/2009 |
| WO | 0138873 A2 | 5/2001 |
| WO | 0206806 A2 | 1/2002 |
| WO | 02097418 A1 | 12/2002 |
| WO | 2005038048 A1 | 4/2005 |
| WO | 2007014931 A | 2/2007 |
| WO | 2008051804 A2 | 5/2008 |
| WO | 2009147093 A1 | 12/2009 |
| WO | 2013065994 A1 | 5/2013 |
| WO | 2013163120 A1 | 10/2013 |

OTHER PUBLICATIONS

International Search Report and Written Opinion of International Application No. PCT/US2013/048108 dated Jan. 16, 2014.
Kim, Sang Kyung, "Redox Cycling for an In-Situ Enzyme Labeled Immunoassay on Interdigitated Array Electrodes", Aug. 2004, Doctoral Dissertation, Georgia Institute of Technology, pp. 1-199.
Paeschke et al., "A Stacked Multichannel Amperometric Detection System", 1995, Kluwer Academic Publishers, Micro Total Analysis Systems—Proceedings of the .mu.TAS '94 Workshop, pp. 249-254.
European Search Report and Opinion of European Application No. EP 161752555 dated Oct. 21, 2016.
Office Action of Russian Application No. 2016128035 dated Oct. 3, 2019.
Jeong-Li Heo, "Development of electrochemical sensors based on carbon interdigitated array nanoelectrodes for high current amplification", 2014, https://core.ac.uk/download/pdf/36622782.pdf, pp. 1-80.
Wolfrum et al., "Electrochemical Redox-Cycling Devices", May 9, 2014, https://core.ac.uk/download/pdf/36622782.pdf, pp. 1-130.

* cited by examiner

READER DEVICE AND METHOD OF SIGNAL AMPLIFICATION

CROSS-REFERENCE TO RELATED APPLICATIONS

This application is a division of U.S. Ser. No. 15/441,518, now U.S. Pat. No. 10,330,630, filed Feb. 24, 2017 which is a continuation of U.S. Ser. No. 14/409,771, filed Dec. 19, 2014 which claims the benefit of U.S. National Stage of International Application No. PCT/US2013/048108, filed Jun. 27, 2013 and claims priority under 35 U.S.C. 119(e) to U.S. Provisional Application No. 61/665,353, filed Jun. 28, 2012. All of the applications are incorporated by reference herein in their entirety.

STATEMENT REGARDING FEDERALLY SPONSORED RESEARCH AND DEVELOPMENT

Not Applicable.

BACKGROUND

A sensor (also called detector) is a device that measures a physical quantity and converts it into a signal which may be read by an observer or by an instrument. For example, a mercury-in-glass thermometer converts the measured temperature into expansion and contraction of a liquid which may be read on a calibrated glass tube. A thermocouple converts temperature to an output voltage which may be read by a voltmeter. For accuracy, most sensors are calibrated against known standards.

In biomedicine and biotechnology, sensors which detect analytes having a biological component, such as cells, protein, or nucleic acid are called biosensors. Biosensors may be used for both in vitro and in vivo applications.

Typically, biosensors may be exposed to a biological specimen, such as blood or urine, and used to detect predetermined analytes within the biological specimen. The biosensor may then be exposed to a transducer or detector element which may work in a physiochemical manner using a sensing medium such as light, electricity, piezoelectric, electrochemical, or the like. In any event, the transducer or detector element transforms a signal from the biosensor into another signal that may be more easily measured and quantified. The signal produced by the transducer or detector element may be provided to a reader device having associated electronics, signal processors, and/or a display to provide the results in a user readable format. For example, the results may be provided on a graphical display.

In biomedicine and biotechnology, the amount of analytes of interest within a sample is very small and difficult to detect. As such, amplification of the signal may provide more accurate reading for a detected analyte. In particular, literature describes one method of signal amplification using oxidation and reduction of a species on a working electrode provided with direct current (DC), which may be imbalanced by holding a working electrode at _200 mV and another electrode at +50 mV. Alternating current (AC), however, is generally not used within the art, and if used, is solely for the determination of adequacy of a sample volume, and the like. See, U.S. Patent Publication No. 2003/0098233, U.S. Patent Publication No. 2006/0175205, U.S. Patent Publication No. 2009/0020439, U.S. Patent Publication No. 2009/0181411, U.S. Patent Publication No. 2011/0284393, U.S. Pat. Nos. 6,843,263, and 7,473,397 which are all hereby incorporated by reference in their entirety.

BRIEF DESCRIPTION OF THE DRAWINGS

The accompanying drawings, which are incorporated in and constitute a part of this specification, illustrate one or more implementations described herein and, together with the description, explain these implementations. In the drawings.

DETAILED DESCRIPTION

The following detailed description refers to the accompanying drawings. The same reference numbers in different drawings may identify the same or similar elements.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements, but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the inventive concept. This description should be read to include one or more and the singular also includes the plural unless it is obvious that it is meant otherwise.

Further, use of the term "plurality" is meant to convey "more than one" unless expressly stated to the contrary.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Circuitry, as used herein, may be analog and/or digital, components, or one or more suitably programmed microprocessors and associated hardware and software, or hardwired logic. Also, "components" may perform one or more functions. The term "component," may include hardware, such as a processor, an application specific integrated circuit (ASIC), or a field programmable gate array (FPGA), or a combination of hardware and software. Software includes one or more computer executable instructions that when executed by one or more component cause the component to perform a specified function. It should be understood that the algorithms described herein are stored on one or more non-transient memory. Exemplary non-transient memory includes random access memory, read only memory, flash memory or the like. Such non-transient memory may be electrically based or optically based.

Figure 1:
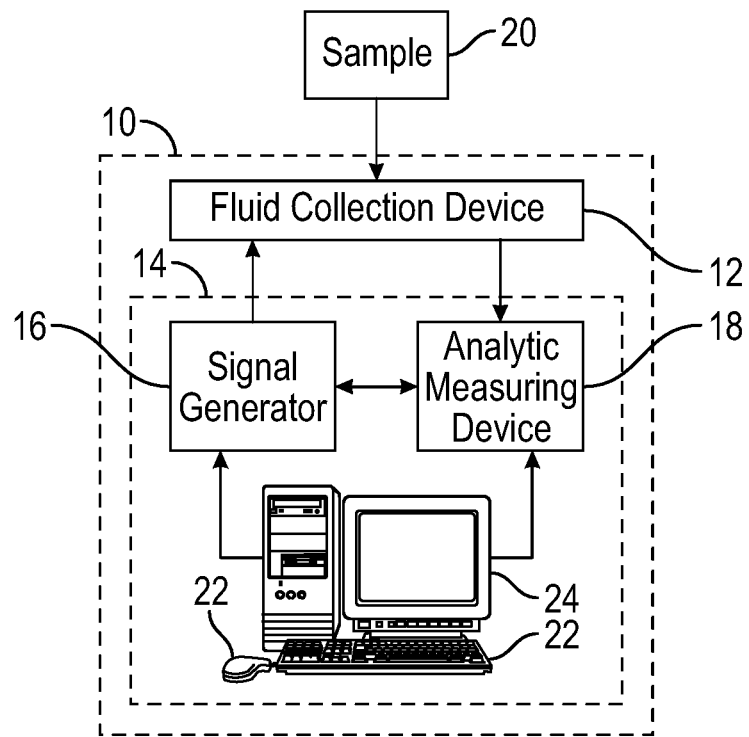
FIG. 1 is a block diagram of a sensor kit constructed in accordance with the present disclosure.

Referring now to the Figures and in particular to FIG. 1, shown therein is an exemplary sensor kit 10 constructed in accordance with the present disclosure. When the sensor kit 10 is used for analyzing biological samples, the sensor kit 10 may be referred to as a biosensor kit. In general, the sensor kit 10 includes one or more fluid collection devices 12, and an analysis instrument 14. Analysis instrument 14 may determine measurement and/or concentration of a given constituent in a sample 20 provided to the one or more fluid collection devices 12. In one embodiment, the fluid collection device 12 can be a test strip. In particular, the analysis instrument 14 may provide alternating current (AC) to the fluid collection device 12 to determine measurement and/or concentration of a given constituent in the sample 20. The alternating current signal may have a voltage and frequency suitable to induce an electric current across electrodes of the fluid collection device 12 to induce redox cycling between the at least two electrodes in order to create an amplified signal which aids in the measurement and/or concentration of the given constituent in the sample 20. During redox cycling, one of the electrodes is a working electrode, and another electrode is a counter electrode. When the alternating current signal is applied to the working electrode and the counter electrode, the working electrode, for example, alternates between a collector mode and a generator mode in rapid succession such that redox cycling occurs in order to produce signal amplification.

As will be described in detail below, the sensor kit 10 can be used within the healthcare industry for detecting measurements and/or concentrations of the given constituent in the sample 20. In this instance, the sample 20 is a biological sample, such as blood, urine or saliva collected from an animal, such as a human, or a non-human (such as a cat, dog, cow, horse, fish, or the like). Alternatively, the sensor kit 10 can be used for detecting non-biological chemicals, such as low level pesticide/agrochemicals in the environment or low level contaminants in water, for example.

The analysis instrument 14 may be provided with one or more signal generators 16 operable to provide an AC signal to the fluid collection device 12, and one or more analytic measuring devices 18 operable to ascertain presence and/or concentration of a given constituent of a biological sample 20 placed on the fluid collection device 12. The signal generator 16 and the analytic measuring device 18 may be a singular component or separate components. Generally, the analytic measuring device 18 may monitor current produced in response to AC current applied by the signal generator 16 across the fluid collection device 12.

In some embodiments, the signal generator 16 may be configured to provide AC signal to one or more electrodes or electrochemical cells of the fluid collection device 12 as described in further detail herein. The AC signal may include a voltage suitable to induce an electric current across at least two electrodes of the fluid collection device 12. For example, in some embodiments, the AC signal may include a voltage of about 200 mV. Additionally, the AC signal provided may be at a low frequency. For example, the AC signal provided may be between approximately 0.1 Hz-15 Hz and preferably between 0.5-2 Hz. Further, it should be understood that it is intended that any and every numeral within any ranges specified herein, including the end points, is to be considered as having been stated. Thus, the range of approximately 0.1 Hz-15 Hz is to be read as indicating each and every possible number in the continuum between 0.1 Hz and 15 Hz.

The analytic measuring device 18 may be configured to ascertain at least the presence and/or concentration of a given constituent in the sample 20. For example, the analytic measuring device 18 may be configured to measure electric current to ascertain the presence and/or concentration of a given constituent in the sample 20. The analytic measuring device 18 may also include circuitry and one or more other devices, such as a printer or a display to provide results of the measurements in a user-perceivable format.

In some embodiments, the analytic measuring device 18 may include a fluid collection device holder or slot for positioning at least one fluid collection device 12 therein. When the fluid collection device 12 is located within the fluid collection device holder for positioning, the analytic measuring device 18 may be in electrical communication with the fluid collection device 12. Holders are well known within the art and need no further description herein.

In some embodiments, the analysis instrument 14 may be provided with one or more input devices 22. The one or more input devices 22 may permit a user and/or machine(s) to provide input into the signal generator 16 and/or the analytic measuring device 18. Exemplary input devices 22 may include, but are not limited to, one or more network port, one or more keyboard (or keypad), one or more touchscreen, one or more mouse, and/or combinations thereof. The analysis instrument 14 may also be provided with one or more output devices 24. The one or more output devices 24 may include, but are not limited to, displays, printers, network ports, and/or the like.

Figure 2:
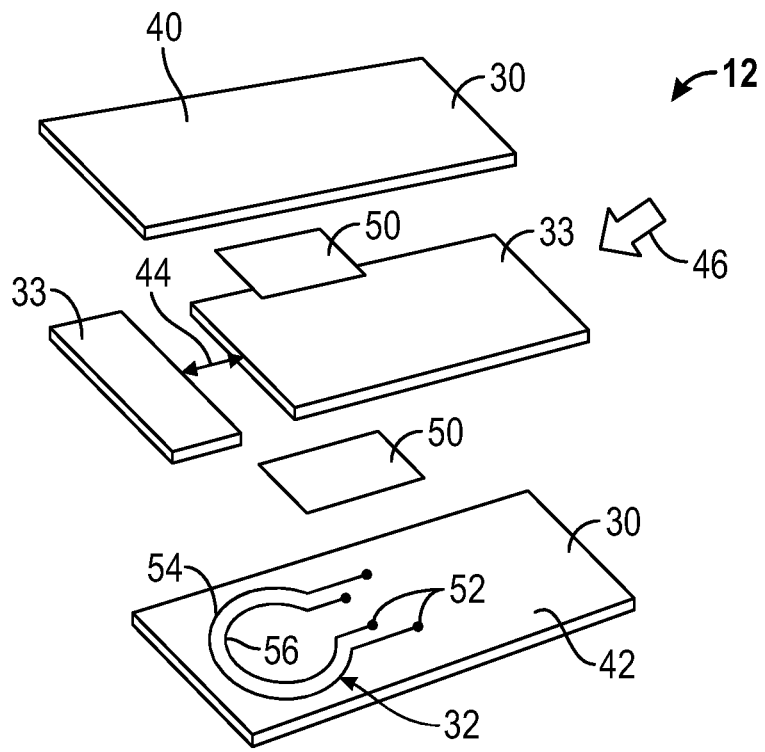
FIG. 2 is an exploded view of an exemplary fluid collection device constructed in accordance with the present disclosure.
Figure 3:
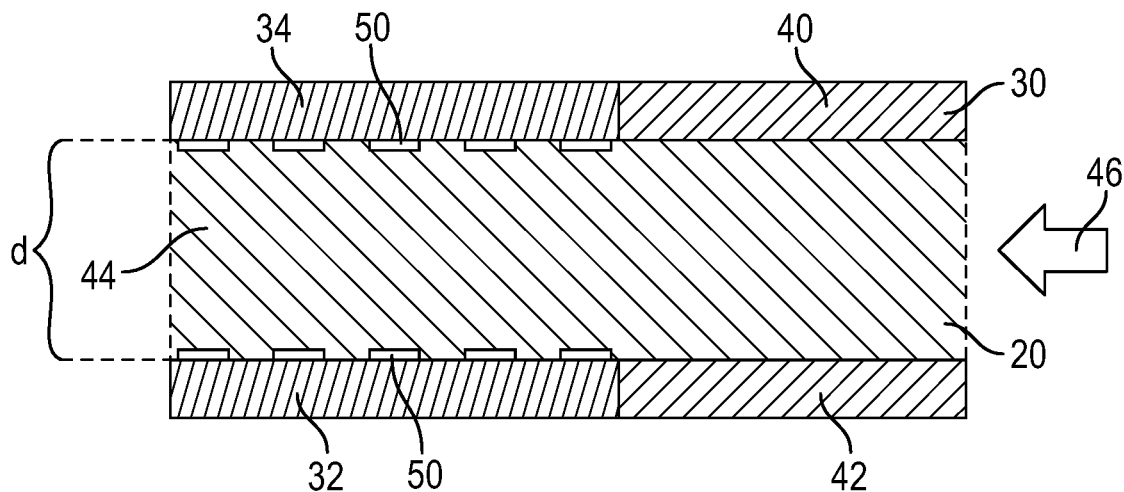
FIG. 3 is a cross sectional view of a portion of a fluid collection device constructed in accordance with the present disclosure.
Figure 4:
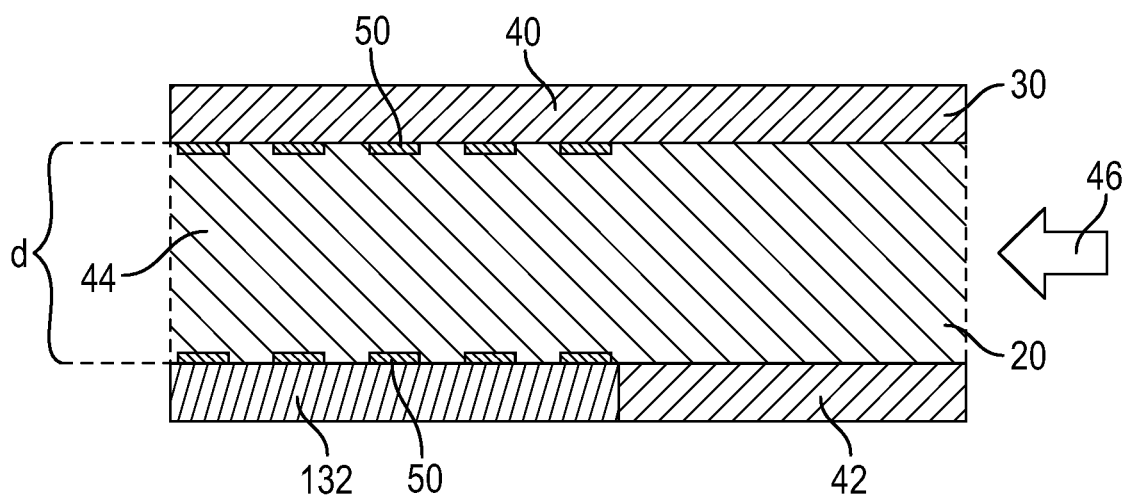
FIG. 4 is a cross sectional view of a portion of another fluid collection device constructed in accordance with the present disclosure.

An exemplary fluid collection device 12 is illustrated in FIGS. 2 and 3. The fluid collection device 12 may be an electrochemical cell-based biosensor. The fluid collection device 12 may include a device 30, a first electrochemical cell 32, and a second electrochemical cell 34. In another embodiment, as illustrated in FIG. 4, the fluid collection device 12 may include the device 30 and a single electrochemical cell 32.

Referring to FIGS. 2 and 3, the device 30 may include a first wall 40 and an opposing second wall 42. The first wall 40 and the second wall 42 may be opposing and may aid in defining a channel 44. The first wall 40 may be spaced apart a distance d from the second wall 42. Optionally, one or more spacer layers 33 may be positioned between the first wall 40 and the second wall 42. Generally, the one or more spacer layers 33 may be thin layers (e.g., less than approximately 200 μm) and, in some embodiments, may also aid in defining the channel 44 as a microfluidic channel. In some embodiments, the one or more spacer layers 33 may be formed of a pressure sensitive adhesive.

In some embodiments, the fluid collection device 12 may include a sample injection port 46 illustrated herein as an arrow. Any sample injection port 46 known within the art or developed in the future may be used as long as it provides at least a portion of the sample 20 to the channel 44. Additionally, one or more additional channels or chambers may be included on or within the fluid collection device 12. For example, one or more channels (e.g., wash chambers, waste port, and the like) known in the art, or developed in the future, may be included on the fluid collection device 12 as long as at least a portion of the biological sample 20 is provided to the channel 44 as described herein.

The device 30 may be constructed of material capable of exposure to the sample 20 including, but not limited to, epidermal cells, blood cells, plasma cells, urine, agricultural chemicals and/or the like, without significant deterioration or adverse results. For example, the device 30 may be selected from a group including, but not limited to, paper, plastics, polymers, and combinations thereof.

The channel 44 may be defined by the first wall 40 and the opposing second wall 42. The channel 44 may aid in retention of at least a portion of the sample 20 positioned and/or injected via a sample application port 46. The sample application port 46 may be in fluidic communication with the channel 44.

One or more enzymes 50 may be deposited on a surface of device 30 within the channel 44. In some embodiments, the one or more enzymes 50 may be coated on the first electrochemical cell 32 and/or the second electrochemical cell 34. Such enzymes 50 may be used within the oxidation/reduction cycle to aid in providing conversion of a given constituent in the biological sample 20 into a specific signal. For example, enzymes may encourage electrons from the given constituent in the sample 20 to transfer to an oxidized form of a mediator molecule, thereby converting it to a reduced formation. Other bio-recognition constituents may also be deposited on the surface binding to the analyte of interest. For example, antibodies, oligonucleotides and the like would allow electrochemical labeling components to reside near or on the surface to allow a specific signal. The mediator molecular may be a small organic or inorganic chemical within the channel 44 that may be capable of existing in both an oxidized and a reduced formation. Mediator molecules generally tend to react quickly to donate or receive electrons. The mediator molecules may in turn provide electrons to the first electrochemical cell 32 and/or the second electrochemical cell 34 of the fluid collection device 12. This series of reactions provides electrochemical measurements capable of review using the analysis instrument 14, illustrated in FIG. 1. Additionally reagents may be included in the fluid collection devices 12. For example, reagents including, but not limited to, preservatives, surfactants, film formers, and the like, may be included in the channel 44 of the fluid collection device 12.

Each electrochemical cell 32 and 34 may include two or more sensor contacts and/or electrodes positioned adjacent to each one another. For example, in FIG. 2, the electrochemical cell 32 includes sensor contacts 52, a first electrode 54, and a second electrode 56 positioned adjacent to the second electrode 54. In some embodiments, the electrodes 54 and 56 may be confined to the area directly adjacent to the channel 44. For example, as illustrated in FIG. 2, the electrodes 54 and 56 do not span the length of the fluid collection device 12, but instead the electrodes 54 and 56 are positioned directly adjacent to the channel 44. For simplicity, the electrochemical cells 32 and 34 will be discussed in reference to electrochemical cell 32 with the understanding that the concepts described herein may apply to the electrodes of the electrochemical cell 34 as further detailed herein.

The electrodes 54 and 56 may be formed of shapes including, but not limited to, circular, square, triangular, rectangular, or any fanciful shape. For example, in FIG. 2, the electrodes 54 and 56 are formed in circular shapes. Although both electrodes 54 and 56 in FIG. 2 are illustrated with similar shapes, each electrode in the electrochemical cell 32 and 34 may be formed in its own individual shape (e.g., circular, fanciful). In some embodiments, the electrodes of each electrochemical cell 32 and 34 may be non-interdigitated. Although electrodes 54 and 56 may generally be non-interdigitated, in some embodiments, electrodes 54 and 56 may be further shaped to increase surface area adjacent to channel 44. Additional electrodes may also be included within each electrochemical cell 32.

In some embodiments, electrodes 54 and 56 may be planar electrodes formed of conductive material. The conductive material may include, but is not limited to, aluminum, gold, silver, copper, carbon nanotubes, graphene, platinum, and/or the like. In some embodiments, electrodes 54 and 56 may be formed on device 30 using techniques including, but not limited to, e-beam evaporation, filament evaporation, electroplating, sputtering, physical vapor deposition (PVD), chemical vapor deposition (CVD), PECVD (plasma-enhanced chemical vapor deposition), atomic layer deposition (ALD), thin film deposition, nano-imprint lithography, jetting, and/or the like Each electrochemical cell 32 and 34 may include one or more molecule receptors for binding to one or more electroactive species within the sample 20 to affect a physical property of the electrochemical cells 32 and 34 upon one or more electroactive species within the sample 20 binding to the one or more molecule receptors.

The molecule receptors of the electrochemical cells 32 and 34 may be positioned on the inside of the channel 44. At least a portion of the molecule receptors may be in fluidic contact with the channel 44. In general, the sample 20 having a given constituent (e.g., analyte) may be brought into contact with a reagent having an enzyme 50 and a mediator within the channel 44. As described herein, mediator molecules in the channel 44 generally tend to react quickly to donate or receive electrons. The mediator molecules may in turn provide electrons to one or more electrochemical cells 32 and/or 34.

As discussed above, the electrochemical cells 32 and 34 may include one or more sensor contacts 52. The sensor contacts 52 may include one or more conductors in electrical communication with electrodes 54 and 56 of the electrochemical cell 32. In some embodiments, the sensor contacts 52 may provide electrical communication between the electrochemical cells 32 and 34, and the analysis instrument 14 illustrated in FIG. 1.

The analytic measuring device 18 of the analysis instrument 14 may receive information detailing loss or gain of electrons providing a quantitative and/or qualitative measurement for analysis. For example, the electron oxidation/reduction cycle may affect the conductivity, resistance and/or capacitance measured across the electrodes 54 and 56. Even further, in embodiments wherein two electrochemical cells 32 and 34 are present, electron binding may affect the conductivity, resistance and/or capacitance measured across the electrochemical cells 32 and 34.

Referring to FIGS. 2 and 4, in some embodiments, the fluid collection device 12 may include a single electrochemical cell 32. The single electrochemical cell 32 may include electrodes providing measurements indicative of the presence and/or concentration of a given constituent of the sample and/or fill detection. Fill detection is generally a manner of determining whether the microfluidic chamber 44 includes a concentration of the sample 20 suitable for providing an accurate and/or precise measurement. Alternatively, visual confirmation of the fill, or additional electrodes (besides those mentioned herein) may be used for fill confirmation.

The design of the single electrochemical cell 32 may include a two-electrode design wherein the first electrode 54 is a counter electrode, and the second electrode 56 is a working electrode as illustrated in FIG. 2. Alternatively, the design of the single electrode 32 may include a four electrode design (e.g. multiple working electrodes (comprising two electrodes), a counter electrode and a reference electrode). In another embodiment, the design of the single electrochemical cell 32 may be constructed as a three electrode design having a counter electrode, a working electrode and a reference electrode. Multiple electrodes may further be added based on design considerations.

The fluid collection device 12 may include a dual electrochemical cell design having a first electrochemical cell 32 and a second electrochemical cell 34 as illustrated in FIG. 3. Generally, the first electrochemical cell 32 may be positioned on the first wall 40 and the second electrochemical cell 34 may be positioned on the second wall 42. The first wall 40 and the second wall 42 may be separated by a distance d. The distance d may influence the signal amplification for detection of presence and/or concentration of a given constituent in the biological sample 20. To increase signal amplification, the distance d may be less than 200 µm. In some embodiments, the distanced may be between 80-100 µm.

In the design of the single electrochemical cell 32 as illustrated in FIG. 4, the electrochemical cell 132 may be solely positioned on the first wall 40 or the second wall 42. For example, in FIG. 4, the single electrochemical cell 132 is positioned on second wall 42. The first wall 40 and the second wall 42 may be separated by a distance d. Confinement of the electrochemical cell 132 within a small space may increase signal amplification for detection of presence and/or concentration of a given constituent in the sample 20. In some embodiments, the first wall 40 and the second wall 42 may be positioned such that the distance d is less than approximately 200 µm. For example, the first wall 40 and the second wall 42 may be positioned such that the distance d is between 50-200 µm.

Figure 5:
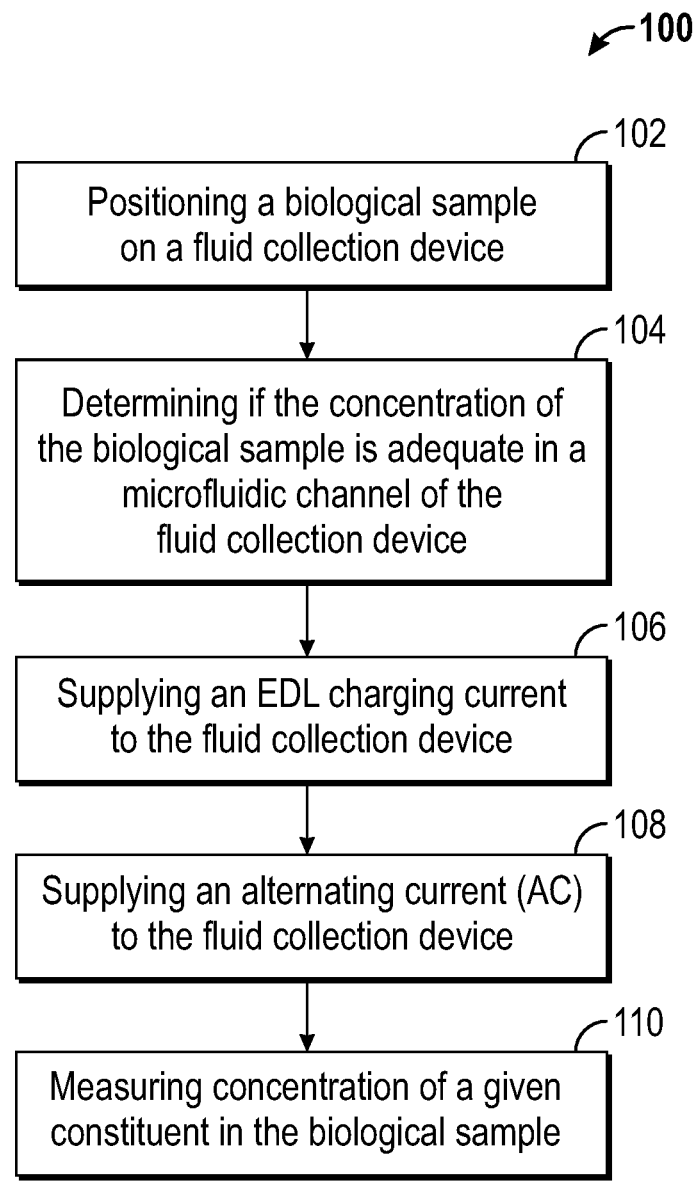
FIG. 5 is a flow diagram illustrating an exemplary method for determining a concentration of a given constituent in a biological sample.

FIG. 5 illustrates an exemplary method 100 for obtaining the presence and concentration of a given constituent of the sample 20 using the sensor kit 10. In a step 102, the sample 20 may be positioned in the sample injection port 46 of the fluid collection device 12. In some embodiments, the sample 20 may travel the through one or more channels or chambers on the fluid collection device 12 prior to arriving in the channel 44. In a step 104, a fill detection method may be used to determine if the concentration of the sample 20 is adequate within the channel 44 for an accurate and/or precise result.

In a step 106, an EDL charging current may be supplied from the signal generator 16 to the first electrochemical cell 32 and/or the second electrochemical cell 34. EDL stands for "Electric Double Layer", which is a region (~0.1-10 nm) at an interface between the electrodes 54 and 56 and an electrolyte within the sample 20 where the electrolyte takes on a local charge. Alternating current sensor analysis may neglect any current that would be measured from the changing electric field (e.g., EDL charging current). In other words, when the potential in the electrodes 54 and/or 56 changes, an electric field across the electrode/electrolyte interface (EDL) also changes forming a time varying electric field having an associated current (called 'displacement current' or 'charging current') that is measurable by the analytical measuring device 18 even without the presence of the electrochemical reaction. Neglecting the EDL charging current can enable recognition of an analyte with less signal background interference and with reduced measurement time due to the time dependence usually associated with the EDL charging current. Analysis of the subsequent electron transfer kinetics may also be enhanced due to the lack of interference of the EDL charging current allowing more specific analysis and signal reports of such analytes.

In some embodiments, multiple signal generators 16 may be used. For example, a first signal generator 16 may provide AC to the first electrochemical cell 32 and a second signal generator 16 may provide AC to the second electrochemical cell 34. In this regard, the signal generator 16 may provide signals out of phase (i.e., asynchronous) between the two electrochemical cells 32 and 34 or in the same phase (i.e., synchronous).

Once AC is applied to the first electrochemical cell 32 and/or the second electrochemical cell 34, the oxidation/reduction cycle of the given constituent of the sample 20 may occur providing a measureable reading for the analytic measuring device 18. In a step 110, the analytic measuring device 18 may perform an analysis to provide the concentration of the given constituent of the sample 20. In some embodiments, amperometric analysis may be performed. In other embodiments, coulometric or voltammetry analysis may be performed. For example, signal averaging and peak sensing can be applied to a resulting sinusoidal AC response. Further treatment of the signal would allow concentration analysis to the analyte of interest.

The signal generator 16 may also be configured to provide (1) a "rest" step of a predetermined time period, and/or (2) an imbalanced polarity, such as −200 mV switching to +150 mV. The predetermined time period of the rest step may be from 1 to 500 milliseconds, for example before switching the polarity.

In some embodiments, multiple fluid collection devices 12 and readings may be performed to provide calibration of the analysis instrument 14.

To use the analysis instrument 14, the fluid collection device 12 having a biological sample, for example, is introduced to the analysis instrument 14. The fluid collection device 12 can be introduced to the analysis instrument 14 by a user connecting the sensor contacts 52 to contacts or electrodes of the analysis instrument 14. For example, the analysis instrument 14 may have a port (not shown) adapted to receive one or more of the fluid collection devices 12 whereupon insertion of the one or more fluid collection devices 12 into the port, the sensor contacts 52 are automatically connected to the sensor contacts of the analysis instrument 14. As discussed above, the analysis instrument 14 is configured to (1) provide the alternating current signal to at least two electrodes of at least one of the first and second electrochemical cells 32 and 34 of the biosensor interacting with the biological sample of the fluid collection device 12. Further, as discussed above, the alternating current signal has a voltage suitable to induce an electric current across the two electrodes, and (2) measure electric current to ascertain at least one of a concentration and presence of a given constituent of the biological sample.

As another example, the fluid collection device 12 can be read as follows. An alternating current signal can be applied across at least two electrodes of at least one of the first and second electrochemical cells 32 and 34 having the sample 20 applied thereto. The alternating current signal has a voltage and frequency suitable to induce an electric current across the two electrodes to induce redox cycling between the at least two electrodes to create an amplified signal. The current of the amplified signal is measured and correlated with predetermined information to ascertain at least one of a concentration and presence of a given electroactive species of the sample.

The foregoing description provides illustration and description, but is not intended to be exhaustive or to limit the inventive concepts to the precise form disclosed. Modifications and variations are possible in light of the above teachings or may be acquired from practice of the methodologies set forth in the present disclosure.

Also, certain portions of the implementations may have been described as "components" or circuitry that performs one or more functions. The term "component" or "circuitry" may include hardware, such as a processor, an application specific integrated circuit (ASIC), or a field programmable gate array (FPGA), or a combination of hardware and software.

Even though particular combinations of features are recited in the claims and/or disclosed in the specification, these combinations are not intended to limit the disclosure. In fact, many of these features may be combined in ways not specifically recited in the claims and/or disclosed in the specification. Although each dependent claim listed below may directly depend on only one other claim, the disclosure includes each dependent claim in combination with every other claim in the claim set.

No element, act, or instruction used in the present application should be construed as critical or essential to the invention unless explicitly described as such outside of the preferred embodiment. Further, the phrase "based on" is intended to mean "based, at least in part, on" unless explicitly stated otherwise.

What is claimed is:

1. An analysis instrument, comprising:
a first signal generator providing a first alternating current signal having a first frequency within a range between 0.5 Hz to 2.5 Hz, the first alternating current signal varying from a positive voltage to a negative voltage, the first signal generator supplying the first alternating current signal to at least two electrodes of a first electrochemical cell of a sensor to switch polarities of the electrodes, the electrodes including bio-recognition constituents binding to an analyte of interest, the bio-recognition constituents selected from a group consisting of antibodies, oligonucleotides, and molecule receptors for binding to one or more electroactive species, the first alternating current signal having a first voltage and a first frequency suitable for inducing redox cycling between the at least two electrodes in which one of the electrodes is a working electrode and another of the electrodes is a counter electrode to create a first amplified signal across the two electrodes; and
a second signal generator configured to provide a second alternating current signal to at least two electrodes of a second electrochemical cell of the sensor, the second alternating current signal having a second voltage and a second frequency suitable to induce redox cycling across the two electrodes of the second electrochemical cell to generate a second amplified signal; and
an analytical measuring device to ascertain at least one presence and concentration of a given constituent of a sample by measuring the first amplified signal and the second amplified signal.

2. The analysis instrument of claim 1, wherein the first signal generator and the second signal generator are synchronized to provide the first alternating current signal and the second alternating current signal in a same phase.

3. The analysis instrument of claim 1, wherein the first signal generator and the second signal generator are asynchronous to provide the first alternating current signal and the second alternating current signal out of phase.

4. The analysis instrument of claim 1, wherein the second frequency is within a range between 0.5 Hz to 2.5 Hz.

5. The analysis instrument of claim 1, wherein the first signal generator and the second signal generator are synchronized to provide the first alternating current signal and the second alternating current signal in a same phase, and wherein the second frequency is within a range between 0.5 Hz to 2.5 Hz.

6. The analysis instrument of claim 1, wherein the first signal generator and the second signal generator are asynchronous to provide the first alternating current signal and the second alternating current signal out of phase, and wherein the second frequency is within a range between 0.5 Hz to 2.5 Hz.

7. The analysis instrument of claim 1, wherein the first signal generator is configured to provide a "rest" step of a predetermined time period before switching polarity.

8. The analysis instrument of claim 1, wherein the first signal generator provides the first voltage with an imbalanced polarity.

9. The analysis instrument of claim 1, wherein the first electrochemical cell is provided on a first wall, and the second electrochemical cell is provided on a second wall so as to oppose the first electrochemical cell, and wherein the first electrochemical cell and the second electrochemical cell are separated by a channel.

10. The analysis instrument of claim 9, wherein the second frequency is within a range between 0.5 Hz to 2.5 Hz.

11. The analysis instrument of claim 9, wherein the first signal generator and the second signal generator are synchronized to provide the first alternating current signal and the second alternating current signal in a same phase, and wherein the second frequency is within a range between 0.5 Hz to 2.5 Hz.

12. The analysis instrument of claim 9, wherein the first signal generator and the second signal generator are asynchronous to provide the first alternating current signal and the second alternating current signal out of phase, and wherein the second frequency is within a range between 0.5 Hz to 2.5 Hz.

13. The analysis instrument of claim 9, wherein the first signal generator is configured to provide a "rest" step of a predetermined time period before switching polarity.

14. The analysis instrument of claim 9, wherein the first signal generator provides the first voltage with an imbalanced polarity.

15. The analysis instrument of claim 9, wherein the the first electrochemical cell and the second electrochemical cell are separated by a distance in a range from 50 micrometers to 200 micrometers.

16. The analysis instrument of claim 1, wherein the the first electrochemical cell and the second electrochemical cell are separated by a distance in a range from 50 micrometers to 200 micrometers.

17. The analysis instrument of claim 16, wherein the second frequency is within a range between 0.5 Hz to 2.5 Hz.

18. The analysis instrument of claim 16, wherein the first signal generator and the second signal generator are synchronized to provide the first alternating current signal and the second alternating current signal in a same phase, and wherein the second frequency is within a range between 0.5 Hz to 2.5 Hz.

19. The analysis instrument of claim 16, wherein the first signal generator and the second signal generator are asynchronous to provide the first alternating current signal and the second alternating current signal out of phase, and wherein the second frequency is within a range between 0.5 Hz to 2.5 Hz.

20. The analysis instrument of claim 16, wherein the first signal generator provides the first voltage with an imbalanced polarity.

* * * * *